US008635084B2

(12) United States Patent
Phillips

(10) Patent No.: US 8,635,084 B2
(45) Date of Patent: Jan. 21, 2014

(54) SYSTEM AND METHOD OF CONDUCTING TELEMEDICINE SESSIONS ACROSS DIFFERENT GEOPOLITICAL ZONES

(75) Inventor: Clinton Glen Phillips, Houston, TX (US)

(73) Assignee: Innovation Specialists LLC, Houston, TX (US)

( * ) Notice: Subject to any disclaimer, the term of this patent is extended or adjusted under 35 U.S.C. 154(b) by 160 days.

(21) Appl. No.: 12/977,220

(22) Filed: Dec. 23, 2010

(65) Prior Publication Data

US 2012/0166221 A1 Jun. 28, 2012

(51) Int. Cl.
*G06Q 10/00* (2012.01)
*G06Q 50/00* (2012.01)

(52) U.S. Cl.
USPC .................................................. 705/2; 705/3

(58) Field of Classification Search
USPC .......................................................... 705/2, 3
See application file for complete search history.

(56) References Cited

U.S. PATENT DOCUMENTS

| 7,590,550 | B2 | 9/2009 | Schoenberg | |
|---|---|---|---|---|
| 2002/0019751 | A1* | 2/2002 | Rothschild et al. | 705/3 |
| 2005/0149364 | A1 | 7/2005 | Ombrellaro | |
| 2005/0251421 | A1* | 11/2005 | Chang et al. | 705/2 |
| 2008/0275311 | A1* | 11/2008 | Haq | 600/300 |

OTHER PUBLICATIONS http://www.apapracticecentral.org/advocacy/state/telehealth-slides.pdf Telehealth 50 State-Review Mar. 2010.*
Dunn et. al., "An Evaluation of Four Telemedicine Systems for Primary Care", Health Services Research; Spring 1977; pp. 19-29 (11 pages).
Vaughan et. al., "A Client/Server Approach to Telemedicine" in Proc. Annu. Symp. Comput. Appl. Med. Care. 1995: 776-780 (5 pages).

* cited by examiner

*Primary Examiner* — Robert Morgan
*Assistant Examiner* — Maroun Kanaan
(74) *Attorney, Agent, or Firm* — Novak Druce Connolly Bove + Quigg LLP

(57) ABSTRACT

A system and method designed to overcome or work with the geopolitical restraints on medical practice that presently hampers the process of conducting physician patient telemedicine sessions across different geopolitical zones such as different states or different countries. The method uses at least one Internet server and database, which may optionally reside or have an IP address within in the one or more geopolitical zones where the physician is licensed to practice medicine. The database will often contain lists of physician authorizations to conduct telemedicine in various other geopolitical zones, lists of patient telemedicine waivers, as well as information pertaining to the physician's specialty, rating, fee structure, and availability. The database may additionally contain other features such as lists of translator availability and patient electronic health records. The server may additionally facilitate video conferencing by presenting a unified user interface and/or relaying video teleconferencing data packets between participants.

20 Claims, 7 Drawing Sheets

Figure 4

Physician search: Availability of General Practitioners and Internists available 10/14 for an online telemedicine consult with State B patients.

Physician Search Results 400

402

| OK | Specialty | Name | Location | Availability | Rate | Language | Rating |
|---|---|---|---|---|---|---|---|
| | GP | Dr Fred MD | State B | 10/14 No | $80 | English | *** |
| | GP | Dr Gail MD | State B | 10/14 No | $80 | English Spanish | ** |
| X | GP | Dr Sam MD | State A | 10/14 Yes | $80 | English | **** |
| | I | Dr Yu MD | State A | 10/14 Yes | $120 | English Mandarin | *** |
| | GP | Dr Me MD | State C | 10/14 No | $80 | English | ** |
| | I | Dr Sue MD | State D | 10/14 No | $110 | English French | ** |

No physicians meeting your criteria are available on 10/14 in your state A. You have selected a telemedicine session with out of state physician Dr. Sam MD, currently licensed in State B, with authorization to practice telemedicine in your state. Do you wish to proceed Yes ● No○ . Release your Electronic Medical Records to Dr. Sam? Yes ● No○ .

| OK | Specialty | Name | Location | Availability | Rate | Language | Rating |
|---|---|---|---|---|---|---|---|
| X | GP | Dr Sam MD | State A | 10/14 Yes | $80 | English | **** |

You have selected Dr. Sam MD. Dr. Sam's only listed languages are English, and you have previously stated that your native language is Vietnamese. Do you also want to schedule a Vietnamese – English Interpreter? Yes ● No ○

500 — Available translators:

| OK | Name | Location | Availability | Rate | Languages | Rating |
|---|---|---|---|---|---|---|
|  | Mr Tran | State A | Yes | $25 | English Vietnamese | *** |
| X | Ms Le | State B | Yes | $30 | English French Vietnamese | **** |
|  | Mr. Phan | State D | Yes | $28 | English Vietnamese | *** |
|  | Mrs Bui | State D | Yes | $32 | English Vietnamese | **** |

How do you wish to pay? Credit card, Insurance, Employer, Gift card or other?
→ ● ○ ○ ○ — 504
506

SYSTEM AND METHOD OF CONDUCTING TELEMEDICINE SESSIONS ACROSS DIFFERENT GEOPOLITICAL ZONES

BACKGROUND OF THE INVENTION

1. Field of the Invention

The field of the invention is in Internet based medical telecommunications such as telemedicine.

2. Description of the Related Art

The general problem of providing patients with rapid access to appropriate medical specialists has been recognized for many years, and ever since the telephone was popularized, much time and effort has been expended in devising methods to deliver improved telemedicine service.

For example, more than 30 years ago, Dunn et. al., "An Evaluation of Four Telemedicine Systems for Primary Care", Health Serv. Res. 1977, spring (12)(1), 19-29 discussed the utility of examining patients by video. In the 1990's, various client server implementations of telemedicine were also described by Vaughan et. al., "A Client/Server Approach to Telemedicine" in Proc. Annu. Symp. Comput. Appl. Med. Care. 1995: 776-780.

More recently, other workers have continued to refine or rediscover various telemedicine methods. For example, Ombrellaro, in US patent application 2005/0149364 discusses a telemedicine system with an integrated electronic medical record, and Chang, in US patent application 2005/0251421 discusses providing interpreter assisted video interpretation systems in a healthcare setting. More recently Schoenberg, in U.S. Pat. No. 7,590,550 teaches a computerized directory method of establishing an immediate real-time communications link between a patient and a physician.

In spite of these advances, telemedicine is still seldom used at present, suggesting that further progress is desirable. In particular, one problem that continues to limit patient access to medical care is the fact that at present, telemedicine systems are generally only authorized within the confines of a particular geopolitical area (e.g. geographic zone of healthcare provider licensing), such as a specific United States State, or a specific country. This limits patient access to only the healthcare providers that are located within the patient's particular geopolitical zone of residence. In the event that no healthcare providers with a suitable specialty, interest in providing telemedicine service, and availability schedule can be found within the patient's particular geopolitical zone of residence, then the patient's need for medical services may be frustrated.

At the same time, outside of the patient's particular geopolitical zone, there may be other healthcare providers who have the proper specialization, interest in providing telemedicine services, and who may have room in their schedule for another patient. Thus the present state of affairs for telemedicine is presently suboptimal due to the artificial constraints of the present geopolitical based system of healthcare provider licensing.

BRIEF SUMMARY OF THE INVENTION

In one embodiment, the invention may be a system and method designed to overcome or work with the geopolitical restraints on medical practice that presently hampers conducting physician patient telemedicine sessions across different geopolitical zones. The invention uses at least one Internet server and database, which may optionally reside in or have an IP address within the one or more geopolitical zones where a healthcare provider is licensed to practice medicine. This database will often contain lists of healthcare provider authorizations to conduct telemedicine in various other geopolitical zones, lists of patient waivers consenting to telemedicine consultations with healthcare providers in different geopolitical zones, as well as information pertaining to the healthcare provider's specialty, rating, fee structure, schedule, language, and availability, as well as other special interest tags such as particular sub-specialties (e.g. sports medicine for a particular sport), a particular healthcare center affiliation, and personal characteristics such as age, sex, marital status, parental status. The database may additionally contain other features and data useful for telemedicine sessions such as lists of available translators, payment information, and patient electronic health records. The server may additionally facilitate video conferencing by presenting a unified user interface and/or relaying video teleconferencing data packets between participants.

More specifically, the invention may be a method of conducting Internet based telemedicine between healthcare practitioners and patients residing in different geopolitical zones. This method will generally include acquiring a first set of legal authorizations or permissions that will enable or give permission to healthcare practitioners who are licensed in a first set of geopolitical zones (e.g. an American state such as Nevada, or alternatively a separate country such as Canada) to conduct telemedicine sessions with patients who themselves reside in a second set of geopolitical zones (e.g. an American state such as California). The method will also generally include acquiring a second set of legal waivers from these patients (who reside in this second set of geopolitical zones such as California) consenting to telemedicine sessions with at least some of the healthcare practitioners who are licensed in the first set of geopolitical zones (e.g. Nevada, Canada).

Using this method, and internet server database will be constructed that comprises data from these healthcare practitioners, their first set of legal authorizations, these patients, and their second set of legal waivers. This internet server based database will often also comprise the specialties and specialties and availability schedules of at least some of these healthcare practitioners. Using the method, a patient residing in a second geopolitical zone (e.g. California) may contact this internet server based database using the user interface of an Internet connected computational device. Here this may be, for example, a web browser running in the graphical user interface of an Internet network connected computer, or alternatively the browser running in the graphical user interface of a smart cellular phone. These devices will often usually have audio and video pickups (sensors, cameras) as well, so as to facilitate remote video teleconferencing. The patient(s) may use their Internet connected computational devices to transmit their current health status to the Internet server based database. Thus, for example, if the patient is healthy but has high blood pressure and wants a consultation, the patient may transmit this fact. The Internet server based database will generally have a search engine capable of matching the patient current health status with the specialties and availability schedules of at least some of the various healthcare practitioners in the database, thus generating match information. The internet server and database will then provide at least some of this match information back to the patient. The patient may then use this match information to select an appointment time to schedule a telemedicine session with one or more available healthcare practitioner(s). Generally, this Internet server based database will also contain at least the audio-video link information required to establish audio and video communication between the patient and the healthcare practitioner, and this Internet server based database will transmits this audio-video link information to the patient and healthcare practitioner on or before the time of the scheduled telemedicine session. The system may also perform other functions as needed, such as scheduling third parties such as interpreters, managing patient electronic health records, doing more elaborate searching and matching between patent and healthcare practitioner, and also managing various payment methodologies, including direct payments, as well as third party payments including payments from employers, the government, and even gift certificates from private third party payers.

BRIEF DESCRIPTION OF THE DRAWINGS

FIG. 4 shows an example screen shot for a patient search result for a physician who can schedule a telemedicine session on a day several days in the future, such as trying to book a date for a telemedicine session on October 14 when the present date is October 12.

FIG. 5 shows an example screen shot for a patient search for an interpreter with a suitable availability and language capability, as well as an example of a payment field.

DETAILED DESCRIPTION OF THE INVENTION

Figure 1:
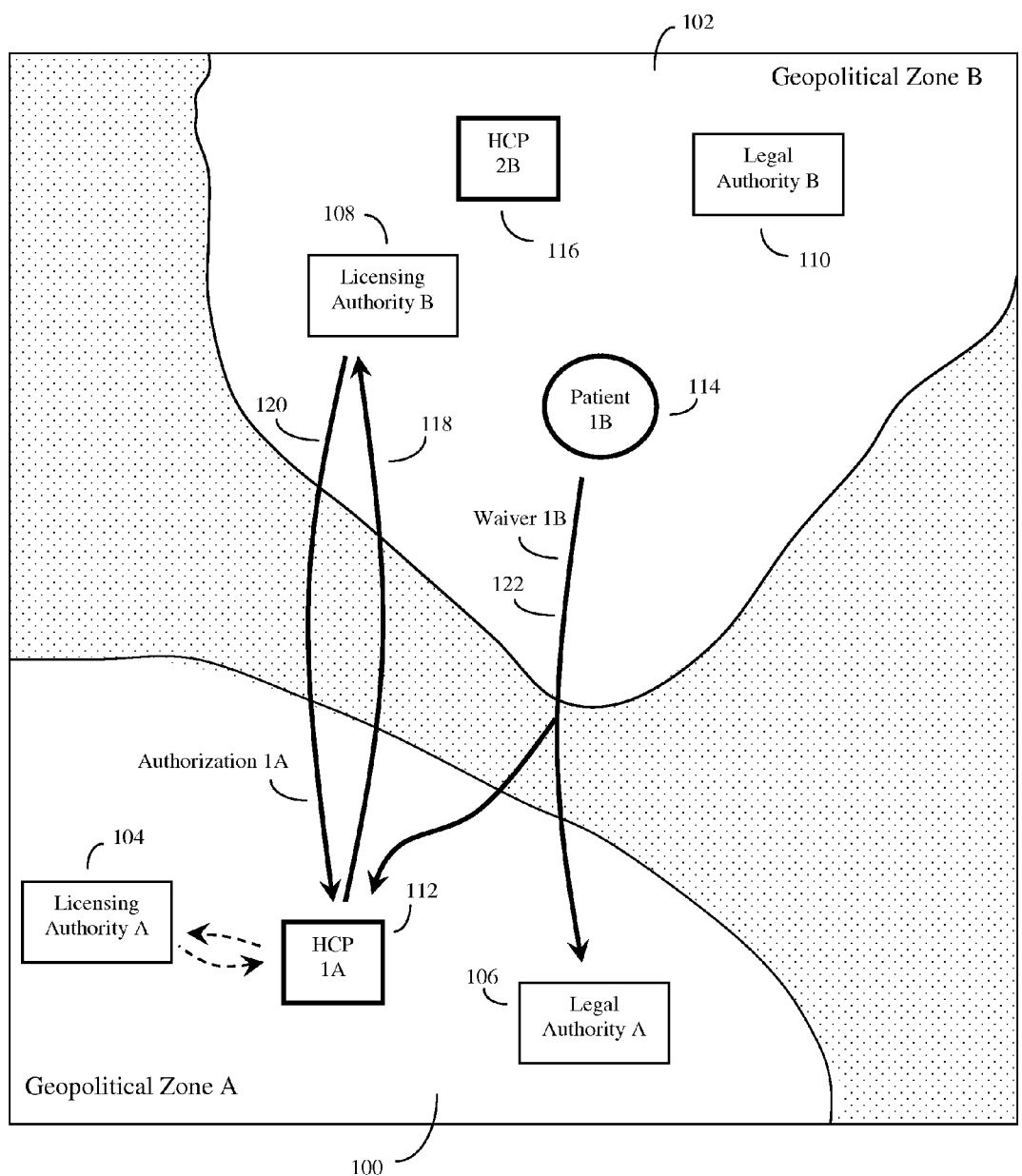
FIG. 1 shows a patient and healthcare provider residing in different geopolitical zones, along with an authorization and waiver process.

Nomenclature: In this disclosure, often the terms healthcare provider and healthcare practitioner (HCP) will be used interchangeably, and physicians and physician specialists will often be used as a specific example of one type of healthcare provider/practitioner.

Equipment and software: The system and methods of this invention are intended to be implemented using computer based servers, often powered by multiple computer processors from the x86 family (e.g. Intel or AMD processors), usually running operating systems such as Windows, Linux, Unix, or other standard operating systems, and usually having many gigabytes of random access memory. The servers will typically be connected to mass storage devices, such as disk drives, also capable of storing many gigabytes of data. The system and methods of the invention will often be implemented in the form of software, such as database management software (e.g. SQL software which may run under popular database management programs such as MySQL or other systems such as Oracle), web server software such as Apache, programming languages for dynamic web pages such as PHP, Perl, Python, as well as other web application framework languages and systems languages such as Ruby on Rails, and the like. The server(s) will often then be connected to suitable networks such as the Internet, often by high bandwidth connections. In some embodiments, at least one server will reside in each geopolitical zone serviced by the system, and these geopolitical zone assigned servers may be connected to one or more master servers that span multiple geopolitical zones. Thus for example, healthcare providers in one geopolitical zone may be represented by a server geographically located in the healthcare provider's particular geopolitical zone. A patient residing in a different geopolitical zone may be routed by either a server spanning multiple geopolitical zones, or a server in the patient's own geopolitical zone, to the server specialized to the healthcare providers geopolitical zone of licensing, and subsequent transactions may then take place using the server that is geographically localized to the healthcare providers geopolitical zone of licensing.

The patient and healthcare providers will normally interact with the telemedicine service using standard computerized devices capable of Internet communications, often using standard web browsers (e.g. Windows Explorer, Firefox, Chrome, Safari and the like) running on standard operating systems such as Windows, Linux, iOS and the like. Normally these systems will be equipped with standard graphical user interfaces and peripherals capable of displaying audio, video, and text, and receiving audio, video, and text input.

There are two basic ways or modes in which a patient living in a first geopolitical zone, such as a state (for example California) may be given a telemedicine consultation by a physician or healthcare provider who is licensed in a second geopolitical zone (such as Nevada). The first way is for the patient to travel from his or her state of residence to the geopolitical zone where the healthcare provider is licensed, and the second way is for the necessary set of legal authorizations and waivers to be exchanged so as to enable the cross-geopolitical zone medical consultation to legally take place.

The invention can also operate in these two basic ways or modes. In one mode, the invention may enable a form of "virtual travel" that, to all practical purposes, induces a state of awareness and consent process similar to the state of awareness and consent that a patient would normally experience upon leaving his or her normal state or geopolitical zone of residence, and traveling to healthcare provider's geopolitical zone of licensure. In an alternative mode, the invention may both facilitate and maintain a database that keeps track of the necessary set of authorizations and waivers necessary to create the proper legal permissions to conduct telemedicine across geopolitical zones. Often, it may be useful to combine the two approaches or modes, so that both the proper set of authorizations and waivers is maintained, and additionally the patient is exposed to a form of virtual travel during at least the initialization of the telemedicine session so that the patient clearly understands the implications of dealing with a healthcare provider in another geopolitical zone (for example, that if the patient wishes to seek local help, then the patient should expect to use an alternate, local healthcare provider).

As previously discussed, when the first, virtual travel mode of conducting across geopolitical zone telemedicine is used, in addition to providing suitable visual or user interface simulations of virtual travel to the patient, it may optionally also be useful to locate the telemedicine server that coordinates the various telemedicine permissions in the same geopolitical zone as the healthcare provider. This ensures that the local geopolitical zone authorities, such as the medical license board and or local governmental authorities can have proper jurisdiction over the server that is coordinating the particular telemedicine session in question, and if necessary shut it down or request disclosure of the contents as necessary and in keeping with the local authorities responsibility for the welfare of the residence of this particular geopolitical zone.

When used in the second, permissions exchange mode, the invention may be a method of conducting Internet based telemedicine between healthcare practitioners (e.g. physicians, physician specialists, nurses, and other healthcare providers) and patients residing in different geopolitical zones, such as different states or countries. Here, as previously discussed, the invention is based on a network connected computerized database, such as an Internet server or web server, that may store a first set of legal authorizations enabling healthcare practitioners licensed in a first set of geopolitical zones to conduct telemedicine sessions with patients residing in a second set of geopolitical zones. For example, physicians with medical licenses in Nevada (geopolitical zone A) may request authorizations from another state, such as California (geopolitical zone B), for the limited purposes of conducting telemedicine sessions for various California residents. Such authorizations may be granted by either the California state medical licensing boards, or alternatively by one or more agencies of the California state government, and may for example be part of a reciprocity agreement with the other geopolitical zone wherein, for example, California physicians are also allowed to apply for legal authorizations to treat Nevada residents.

In an alternative embodiment, a healthcare accrediting organization that accredits healthcare providers/practitioners for telemedicine, and which operates over multiple geopolitical zones, may be used to provide the first set of legal authorizations. This healthcare accrediting organization, which may be a private company, a non-profit organization, or a government or government affiliate might, using America as an example, operate on a national basis and regulate healthcare practitioners across multiple states. Such a multiple geopolitical zone healthcare provider accrediting organization would serve to ensure that the healthcare providers were practicing telemedicine in a responsible manner, and would act to disallow healthcare providers who were, for example, practicing telemedicine on a substandard basis.

At the same time, the invention's network connected computerized database will also store a set of legal waivers from patients, who may be for example, residents of California (Geopolitical zone B) consenting to treatment from physicians or other healthcare providers residing outside of the patient's particular geopolitical zone. Thus a patient living in California may place on record into the database, consent to be treated by a physician or other healthcare provider residing in Nevada.

The invention's network connected computerized database will often also contain a record of the various medical specialties, addresses, contact information, ratings, price information, and availability schedules of various healthcare providers, as well as optional ancillary support personnel and additional optional services such as translators, pharmacies, medical supply houses, home care services, ambulance services, delivery services, and other support services as needed.

Thus when a patient residing in a second geopolitical zone (such as California) contacts the invention's telemedicine internet server based database, for example by using the user interface of an Internet connected computational device (e.g. the keyboard, pressure sensitive display, camera, microphone etc. of a computer, laptop computer, pad computer, cellular telephone, smart cellular telephone), the patient can transmit information pertaining to his or her medical condition (e.g. such as "My blood pressure is up and I want a consultation later this week") to the server and database. The invention's server and database, in addition to sorting for availability of healthcare providers within certain medical specialty, cost, location, availability schedule and rating constraints, can also greatly expand on the range of potential healthcare providers available to the patient by also sorting through the list of healthcare provider authorizations, and may be thus able to better serve the patient by matching the patient up with a healthcare provider in a different geopolitical zone who is more likely to be available.

Given that the invention will often match patients with healthcare providers in different geopolitical zones, it will additionally be useful if the invention's computerized database also contains information, such as the patient's electronic health record, or at least links to the patient's electronic health record, so that the healthcare provider can determine if the patient's particular problems are likely to be within that particular healthcare provider's specialty or sphere of competence. Such electronic healthcare records may conform to common standards, such as the HL7, ANSI X12, CEN-CONTSYS (EN13940), CEN-EHRcom (EN13606), CEN-HISA (EN 12967), DICOM, or other electronic healthcare record standard. Suitable examples of such healthcare standards also include various open source electronic healthcare records such as FreeMED, GNUmed, Hospital OS, HOSxP, Mirth, OpenEMR, OpenMRS, OSCAR McMaster, THIRRA, VistA, and ZEPHRS. Other useful systems and standards include ClearHealth, MedinTux, DHIS, HRHIS, as well as various visualization software such as Drishti Endrov, ITK, InVesalius, ITK-SNAP, MicroDicom, OsriX, ParaView, Voreen, and Xebra. Often the system will include additional levels of privacy checking and patient permissions to help ensure that only authorized individuals may view any particular patient's electronic healthcare record. Additionally, by providing easy access to the patient's electronic healthcare record, healthcare providers who may otherwise be unfamiliar with the patient's particular case can rapidly come up to speed. Similarly, often during or as a result of a particular telemedicine session, additional information may be obtained that should ideally be placed on the patient's electronic health record, even including if necessary audio and/or video information from that telemedicine session. Here the system may provide suitable interfaces and access points to allow the healthcare provider and/or patient to supplement the electronic healthcare record as needed.

Usually, once the patient has entered in his or her current health status (e.g. healthy, exhibiting a particular symptom, needing medication, and so on), the system may then match the up the patient versus the specialties and availability schedules of at least some of the various healthcare practitioners, generate match information, and provide this information the patient to enable the patient to make a relevant selection.

In some situation, the patient may not be totally conversant in the standard language of the physician's geopolitical zone. To return to our previous California-Nevada example, a patient, residing in California, may speak Vietnamese as a first language, and only speak English as a second language with less than optimal ability. In a situation like this, the patient may wish to co-schedule an interpreter at the same time as his or her telemedicine session with the healthcare provider. Here, it will often be useful to collect patient languages of proficiency as part of an initial patient interview or set of menu selection upon the patient's initial enrollment into the system and prior to the patient's routine use of the system. Thus if, for example, in situations where a patient speaking English as a second language requests a telemedicine interview with a healthcare provider who is not proficient in the patient's primary language, then the system may suggest a translator, and either automatically or upon request provide a list of suitable translators for the patient to choose from.

Since telemedicine generally works best when both the physician (healthcare practitioner) and the patient are in simultaneous audio connection and at least one way (patient to physician) video connection (with two way video connection generally being the best, in many embodiments, the system (i.e. the invention's telemedicine server database) will also contain or comprise sufficient audio-video link information to establish audio and video communication between the patient and the healthcare practitioner. Here several options are possible. The server and database may contain both the internet address information for the healthcare practitioner, patient, and any third parties (relatives, interpreters) as needed, and also act to relay the data packets between the parties. Alternatively, the invention's server and database may merely contain address links, such as, for example, for Skype or other online video conferencing systems enabling the patient, healthcare practitioner, and third parties to communicate by third party messaging systems.

In general, in order to insure quality and a consistent user interface, often the invention's server will both present the telemedicine user interface (e.g. present one or more web pages for telemedicine applications), and will also often play a role in relaying the audio and video data packets as well. This can be useful because the system can, as desired, use an encryption method not known to outside users, and thus help protect patient confidentiality during the telemedicine session(s).

FIG. 1 shows a patient and healthcare provider residing in different geopolitical zones, along with an authorization and waiver process. In this diagram, there are two geopolitical zones, geopolitical zone A (100) and geopolitical zone B (102), separated by either a third geopolitical zone or by a geopolitical neutral zone such as a body of water. These geopolitical zones can be different American states or different countries. In FIG. 1, these geopolitical zones are each represented as having a simplified medical-legal structure consisting of a medical licensing authority A (e.g. a state medical licensing board) (104) and legal authority A (such as the state government or courts) (106) for geopolitical zone A and a medical licensing authority B (108) and a geopolitical legal authority B (110) for geopolitical zone B. In this model, healthcare provider HCP 1A (112) who may be a physician or other certified healthcare professional, is licensed to practice medicine in geopolitical zone A but not geopolitical zone B. At the same time, patient 1B (114) is a patient in geopolitical zone B in need of telemedicine services that cannot be quickly or readily provided by other healthcare professionals in geopolitical zone B, such as healthcare provider HCB 2B (116).

To allow telemedicine to legally operate across the different geopolitical zones, at a minimum, it is likely that the healthcare practitioner 1A (112) operating in geopolitical zone A (100) will need to apply (118) for some sort of authorization from the licensing authority B (108) operating in geopolitical zone B (102), and licensing authority B in turn will provide some sort of Authorization 1A certificate (120) allowing at least temporary license or use for telemedicine services, likely under some set of conditions. Additionally, patient 1B (114) in geopolitical zone B will likely at least need to create, sign, or implement some sort of waiver (122). Often this waiver need simply be issued to the geopolitical zone A healthcare professional HCP 1A (112) but at least at some times, such as during litigation, this waiver may also be given to the legal authority A of geopolitical zone A (106) so that, for example, any litigation regarding the telemedicine consult may take place in Geopolitical zone A rather than Geopolitical zone B.

Although such a waiver may make potential litigation less convenient to the patient 1B (114), this waiver will likely be required in order to make it feasible for healthcare practitioner HCP 1A (112) to agree to treat patient 1B (114). Otherwise, it is likely that geopolitical zone A healthcare practitioner 1A (112) will be unwilling to face the prospect of having to defend himself or herself in the courts of geopolitical zone B.

As can be seen, even in this highly simplified case with only two geopolitical zones, two licensing authorities, two legal authorities, one patient and one physician, a considerable amount of "paperwork" or electronic documentation exchange must occur. However in real life, for example in America, there are 50 states, hundreds of thousands of healthcare practitioners, and millions of patients. Thus the process of keeping track of the huge number of permutations of authorizations and waivers is best implemented on a computerized database, ideally accessed by way of an Internet server platform.

Figure 2:
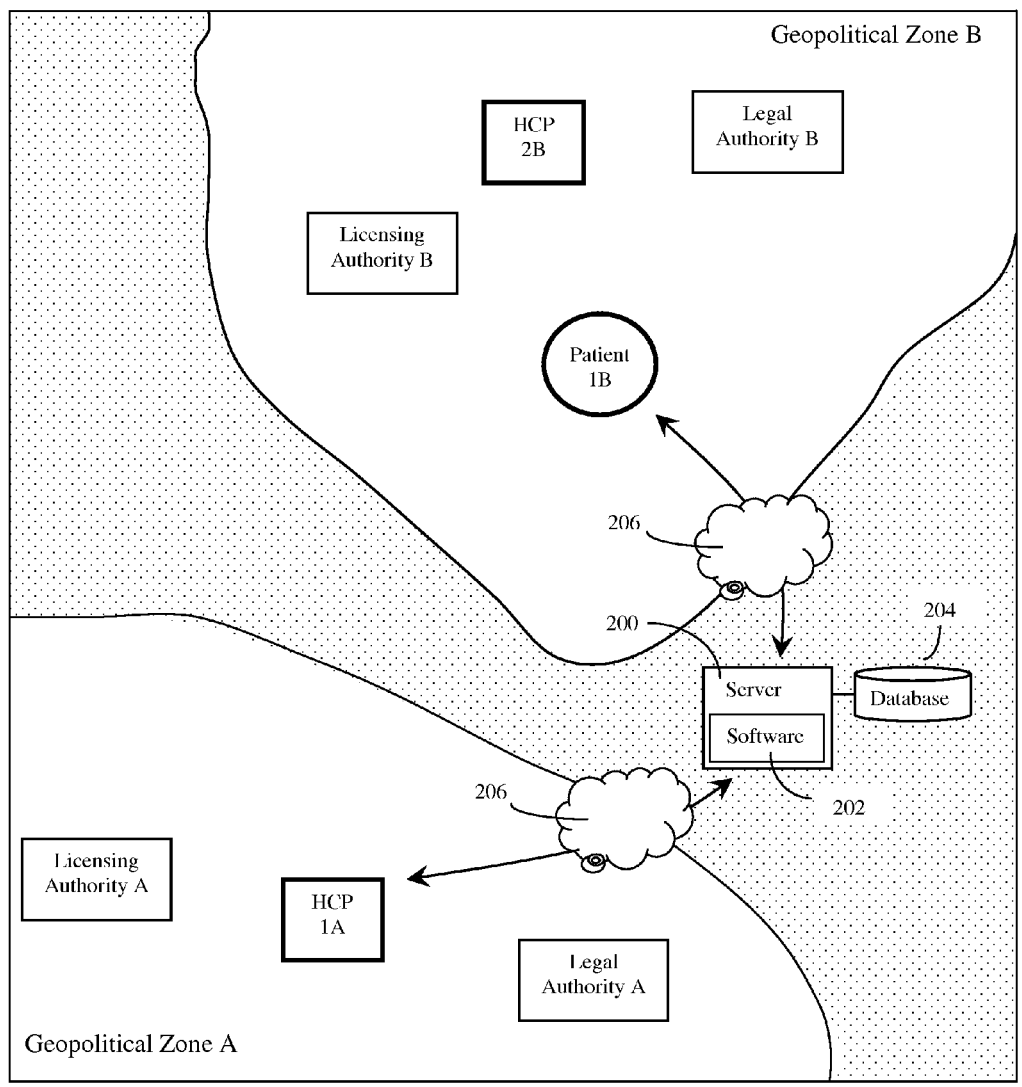
FIG. 2 shows an Internet server, which may be located in different geopolitical zones, and which may contain a database of healthcare practitioner authorizations and patient waivers.

FIG. 2 shows an Internet server (200) suitable for managing some of these previously discussed permutations of authorizations and waivers. As previously discussed, this server will usually contain at least one processor (often multiple processors, such as multiple X86 processors may be used), suitable control and database management software (202), and at least an authorization and waiver database (204) containing multiple healthcare practitioner authorizations and patient waivers. This Internet server will be connected to at least geopolitical zone A and geopolitical zone B by various standard Internet network connections (e.g. optical fiber, Ethernet, satellite communications, telephone lines, cellular network connections) (206). Usually many other geopolitical zones will also be connected in this manner. For example, again using American states, in principle there are many geopolitical zones, including 50 state geopolitical zones plus the District of Columbia, various territories, and even various oversea bases and embassies as well. Other potential geopolitical zones include maritime areas and international areas. In alternative embodiments, different countries may also be represented. For example, a composite telemedicine system using both American states and Canadian provinces may be implemented. In principle any and all countries of the world, with all their different internal sovereign entities, may also participate in this telemedicine system.

Patients and healthcare practitioners alike will usually connect up to the system using various computerized devices such as computers, smart cellular phones, computerized pads, laptops and the like. In some embodiments, patients or physicians may also standard telephone connections as well.

Server (200) may be located or have a geographical associated IP address in various geopolitical zones. In some schemes, the authorizations and waivers will be such as to not impose any constraints on the location or IP address of server (200). In other schemes, the authorizations or waivers may be such as to put constraints on the location or Internet Protocol address (IP address) of server (200). For example, in some situations, it may be preferable to set the IP address of server (200) so as to fall interior to geopolitical zone B, while in other situations, it may be preferable to set the IP address of serer (200) so as to fall interior to geopolitical zone A. Here, the nature of the authorizations and waivers will determine which IP address scheme and server location is preferable. In some situations, it may be necessary to use a plurality of servers (200), so that, for example, one server (200) is located in each geopolitical zone. In this situation, the various additional servers (not shown) may coordinate or exchange data so as to balance the telemedicine loads as best appropriate to the observed patterns of usage.

Figure 3:
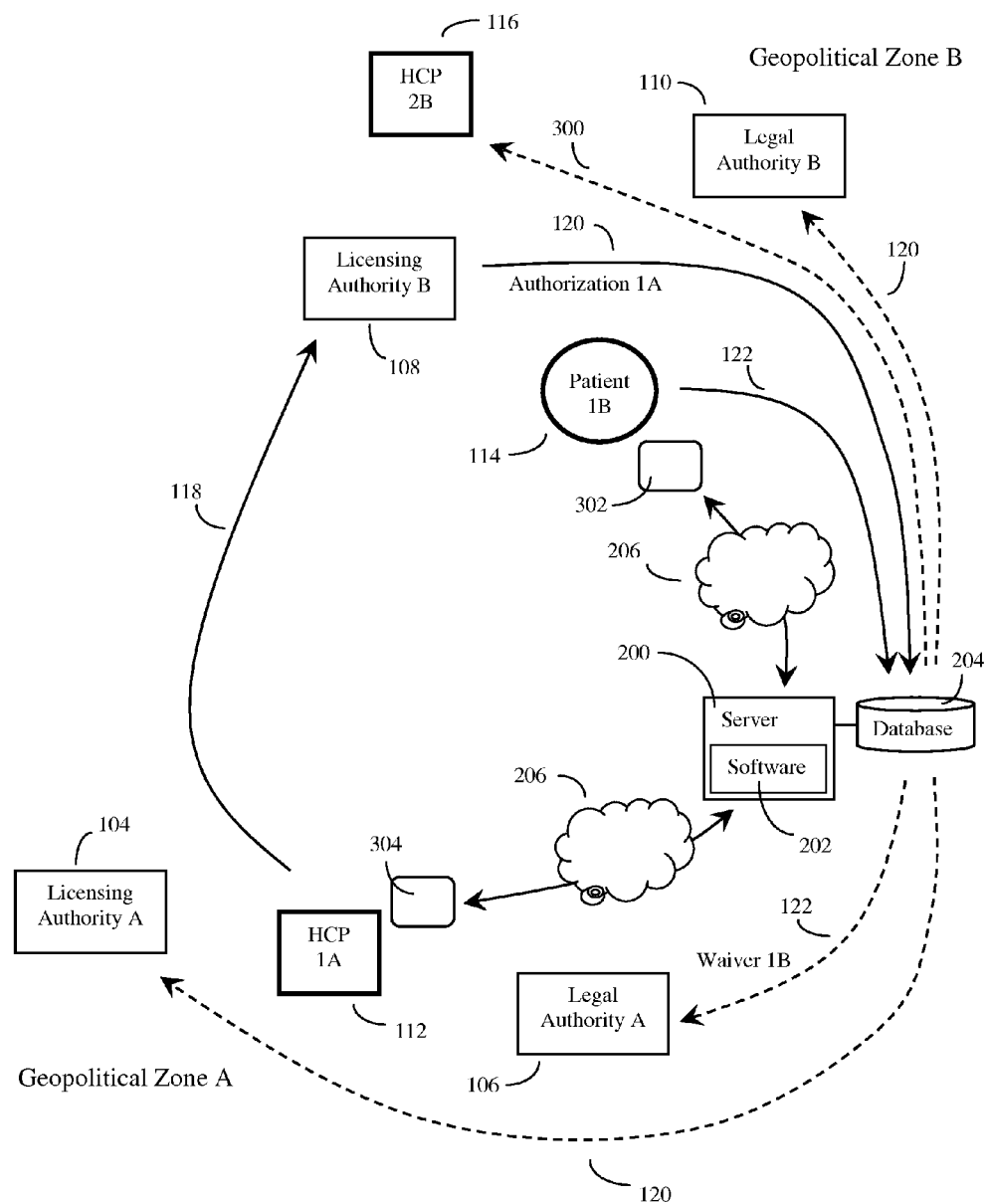
FIG. 3 shows additional details of the authorization and waiver data flow between geopolitical zone B and geopolitical zone B.

FIG. 3 shows additional details some of the various types of authorization and waiver data flow that may occur between geopolitical zone B and geopolitical zone B. As can be seen, Internet server (200), server and database management software (202), and database (204), among many other functions, may store and distribute authorizations and waivers among the various healthcare practitioners, patients, licensing authorities, and legal authorities across the various geopolitical zones. For example, once healthcare practitioner HCP 1A (112) in geopolitical zone A requests authorization from licensing authority B (108) in geopolitical zone B to conduct telemedicine with patients residing in geopolitical zone B, the authorization data 1A (120) can be stored on the database (204), and from there distributed to other interested parties such as the licensing authority A (104) in geopolitical zone A and the legal authority B in geopolitical zone B.

Here the basic principle is one of transparency—that is, the concept that the relevant authorities in both geopolitical zone A and geopolitical zone B will be most likely to cooperate with the telemedicine effort if they are kept fully informed of how the system is operating.

Similarly waivers (122) by patient 1B (114) residing in geopolitical zone B can be also stored on the server (200) database (204), and these waivers in turn can be distributed to various interested parties including the legal authority A (106) in geopolitical zone A, and the healthcare practitioner HCP 1A (112) in geopolitical zone A (previously shown in FIG. 2).

In some embodiments, it may be desirable to set up emergency or backup relationships with healthcare practitioners, such as HCP 2B (116), that reside in the same geopolitical zone as the patient (114). These backup relationships can be used for emergency situations, as well as whenever the remote healthcare practitioner feels that telemedicine is no longer appropriate and local medical assistance is now needed. To facilitate this backup or local medical relationship, the server (200) and database (204) may additionally send information (300) pertaining to the telemedicine session (e.g. patient identity (114), telemedicine healthcare practitioner identity (112), patient electronic medical record, and so on) between patient 1B (114) and remote healthcare practitioner HCP 1A (112) to various local healthcare practitioners such as HCP 2b (116).

As before, the server will often send the information via the Internet or via alternate telecommunications modalities (206). Both the patient(s) (114) and the various healthcare practitioners (112) will communicate and access this information by network connected computerized devices (e.g. devices with at least one computer processor, memory, user interface and a network connection) (302), (304).

Note that in addition to storing authorizations and waivers, database (204), server (200), and software (202) may perform many other functions as well. Some of these additional functions may include storing directory information for the various telemedicine participants, rating and price information, contact information, patient electronic health records, and so on. Additionally, as will be discussed, server (200), software (202) communications link (206) and database (204) may also actively participate in telemedicine sessions by generating suitable web pages and exchanging data packets (e.g. telemedicine audio, video, and text information) between the various participants.

FIG. 4 shows an example screen shot of the user interface (e.g. web page) that the system may generate for a user's computerized device (302) for a patient who has been searching for a patient who is available to schedule a telemedicine conference on short notice (later the same day).

FIG. 4 shows an example of what patient 1B (114) might see on his or her computerized device (302) while accessing server (200) and database (204) over a network such as the Internet (206). Here patient 1B (114) has not yet made a connection with any specific remote healthcare professional, but in this example, may previously given information for the patient's online electronic medical record that may include the patient's native language. In this example, the patient is looking for any reasonable priced and decent quality physician who is a general practitioner or an Internist. Note, of course, that the physician could be one of many other specialties, such as an allergist, dermatologist, gynecologist, medical geneticist, pathologist, psychiatrist, radiologist, surgeon, urologist, and so on. The patient does not particularly care where the physician is physically located, but does want to schedule an appointment quickly, later on that week, which thus limits the number of potential healthcare provider candidates. For this example, assume that the date is October 12, and the patient wishes to schedule a telemedicine conference on October 14.

Here the patient is from geographic zone B which in this example is an American state "B". The results of the search returned by the internet server (200), and displayed on, for example, a web browser of the patient's computerized device (302) is shown as (400). The results show that unfortunately, due to short notice, there are no physicians available for a telemedicine session on October 14 that are from the patient's state of state B. However there are physicians available in other geopolitical zones such as state A, state C, and state D. After looking at the pricing and rating information, the patient has decided to select Dr. Sam MD, (402) a sate A general practitioner (GP), who is available to do a telemedicine session for a competitive price and who is highly rated. The patient has further indicated that he is willing to proceed with an out-of-state physician (404), and has further indicated that he is giving permission to release his electronic medical records to Dr. Sam (406).

Some patients may need translators. In FIG. 5, assume that the patient speaks English as a second language, and Vietnamese as a first language. Since none of the available doctors previously listed in FIG. 4 speaks Vietnamese, the patient has also decided to request the services of an online human translator.

Here the server (200) and database (204) may also contain a record of contact information for available medical translators, and allow the patient to conduct searches. In FIG. 5 (500), the system has asked the patient if he wants a translator, and the patient has answered in the affirmative. The system has provided a list of available translators, and the patient has selected a reasonably priced translator, Ms Le (502), who has a good rating.

The system can also provide the patient with a variety of different payment options, including credit cards, links to third party payors such as insurance plans, relatives, employers, or employer payment plans, and even more unusual options such as gift certificates and gift cards (504). These gift cards may be sold by third parties and can represent a convenient way for relative, friends, and other interested parties to help finance at least part of the patient's telemedicine expenses. Thus a relative might walk into a grocery store and purchase a gift certificate or card as a gift for the patient, or alternatively send in a gift certificate by telephone, mail, or Internet session.

In this example, the patient has decided to pay by the more traditional credit card method (506).

In order to ensure that the patient is fully aware that the healthcare provider they selected is in a different geopolitical zone, in some embodiments of the invention, visual displays of travel may be used.

Figure 6:
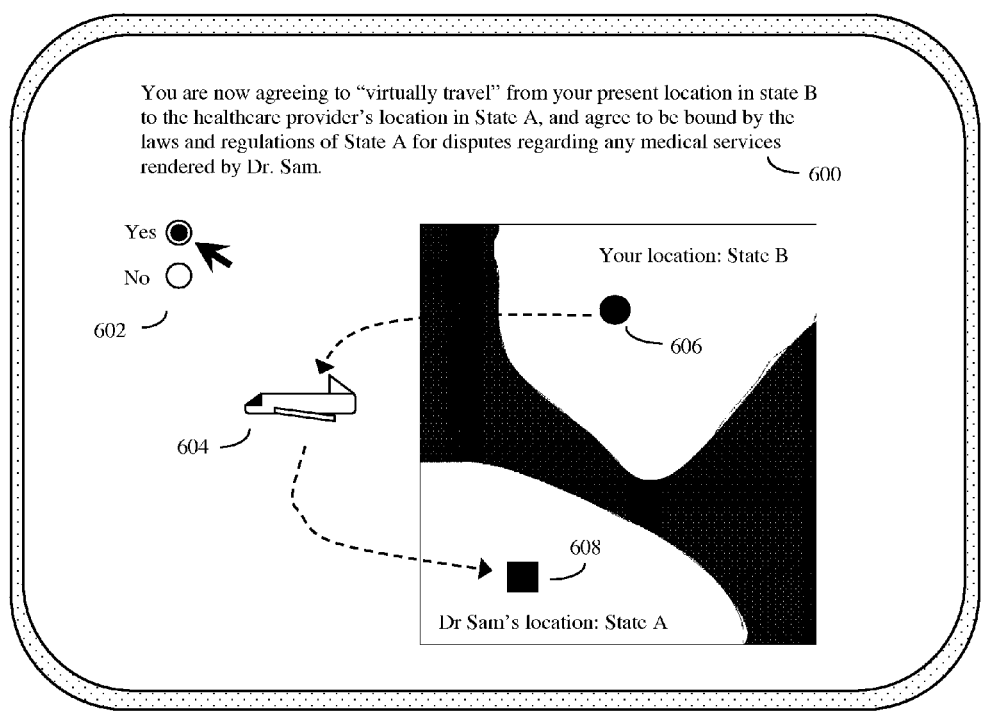
FIG. 6 shows a simulation of travel intended to clearly convey to the patient that the healthcare practitioner is operating from a different geopolitical zone

FIG. 6 shows a simulation of travel intended to clearly convey to the patient that the healthcare practitioner is operating in a different geopolitical zone. The system may both inform the user about the need for "virtual travel" in words (600), request permissions (602), and also show representations of travel such as a display of a vehicle (here a jet) (604) traveling from the patient's current geopolitical zone (606) to the healthcare provider's geopolitical zone (608).

Telemedicine sessions: In some embodiments, the server (200) and database (204) may simply provide contact information (e.g. provide telephone numbers, website addresses, or linkage addresses for third party audio visual applications such as Skype, Google Talk, and the like), and allow the various parties to use whatever communications means they desire. In other embodiments, the server may actively participate in the telemedicine session by, for example, directly relaying the various data packets conveying the audiovisual information between the various parties, and/or by displaying a user interface, such as one or more telecommunications web pages.

Figure 7:
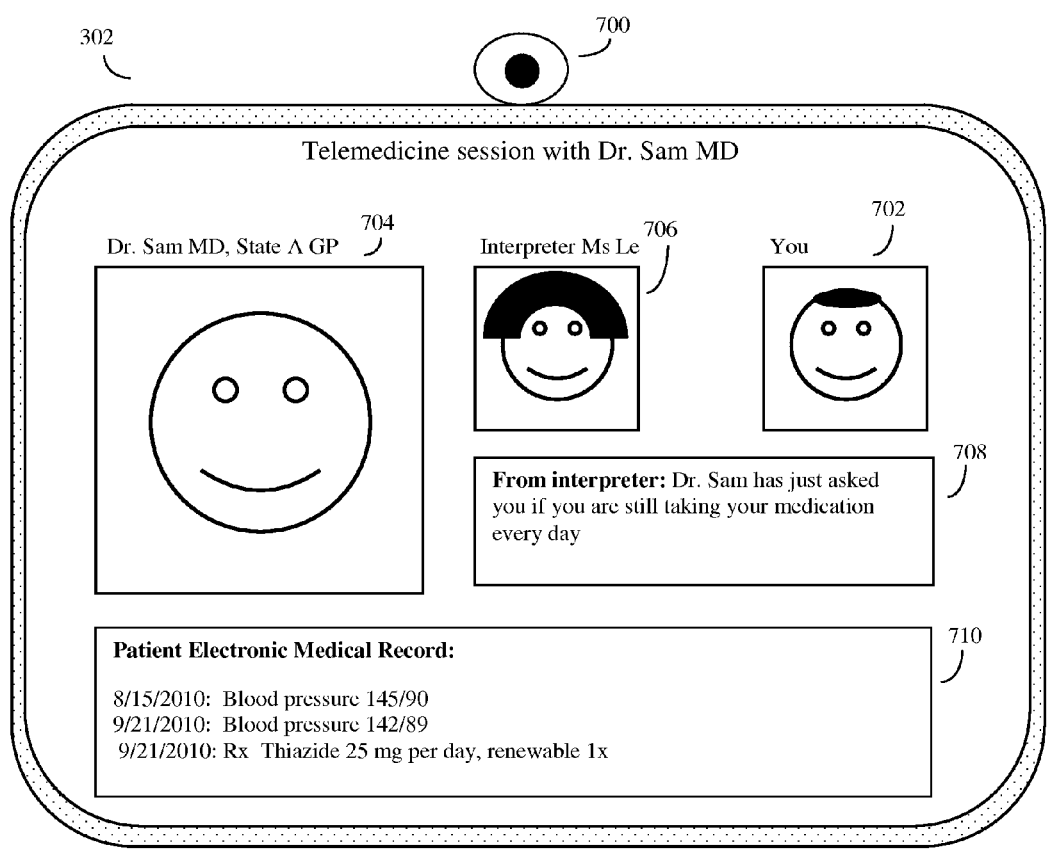
FIG. 7 shows a third party interpreter assisting in a telemedicine session.

FIG. 7 shows a third party interpreter assisting in a telemedicine session. Here the server (200), software (202) and database (204) are providing a telemedicine web page or other user interface and they are also actively relaying the data packets of audio-video information between the various parties.

Here the patient's computerized device may additionally contain at least telemedicine contact information for the respective patients, healthcare providers, and interpreters.

In this example, the patients computerized device (302) has an audio-video pickup, such as a webcam (700), which can provide images and sound of the patient to the patient's healthcare provider (her Dr. Sam MD) and the patient's interpreter (her Ms Le) when needed. The telemedicine user interface can also show the patient what image he or she is transmitting (702).

Here the telemedicine session is showing the patient an image of his or her healthcare provider (704) and interpreter (706). Although it is anticipated that often much of the communications during the telemedicine will be by images and audio (e.g. talking), other channels of information may also be provided. In this example, a first window for supplemental text exchanges between the patient and his or her interpreter is provided (708). A second window for supplemental text or image communications between the patient and the healthcare provider is also shown (710). This second window may be used, for example for communicating certain data to and from the patient's electronic medical record.

In the FIG. 7 example, the patient's blood pressure is being discussed. A portion of the patient's electronic medical record (710) is showing the patient's blood pressure history and blood pressure prescription. The physician (704) is attempting to determine if the patient is taking his medication properly, but the patient has not quite understood the physician's question. Here the interpreter (706) has stepped in to rephrase the question for the patient, and the interpreter has also typed the question into a supplemental text window (708).

Additional Applications:

As previously discussed, in some embodiments, it may be useful to allow telemedicine sessions to be funded by way of gift cards, gift certificates, or other informal third-party reimbursement schemes. For example, children may wish to purchase gift telemedicine sessions for their elderly parents, or parents may wish to schedule telemedicine sessions for sick children who are away from home. Additionally such telemedicine gift certificates may be highly useful for promotional or commercial purposes as well. Example of such gift cards or reimbursement certificates may include:

a) Telemedicine gift certificates from patients to themselves (e.g. to achieve a discount by buying multiple sessions or set amounts of credit with health or medical professionals.)

b) Telemedicine gift certificates from family members and friends (e.g. to help pay for services of loved ones or to encourage them to make use of services with health or medical professionals.

c) Telemedicine gift certificates from strangers. This may be, for example, charity or programs like "pay-it-forward" (asking that a good turn be repaid by doing a good turn for others instead) may encourage people to assist strangers in need, or people who may register on the telemedicine website as being in need of funds for telemedicine services.

d) Telemedicine gift certificates from corporations. In this example, companies will be able to give gift card amounts to employees or valued customers for use on the telemedicine website as partial reimbursement, promotion, or other corporate objective.

e) Telemedicine gift certificates from government entities. Here, for example, the government may choose to give financially or physically-challenged individuals, employees, or other people deemed appropriate gift vouchers (or simply payment vouchers) for use by these individuals as they see fit. In theory, by promoting preventative medicine, such government sponsored telemedicine gift certificates may be come to be viewed as an overall cost savings method because it may help catch medical problems at an earlier stage before these problems become both more serious and more expensive to treat.

Alternative Healthcare Provider Search Algorithms:

As previously discussed, often it will be advantageous for the server and database to provide various types of search services to help ensure that the patient is optimally matched with the proper healthcare provider. More specifically, this search matching process can include, but is not limited to searches involving parameters such as various combinations of:

A—Preferred Language (of the health practitioner or of the translation service)

B—Price Range (e.g. under $100/session; $100-200/session; $200+ per session)

C—Health Concern (e.g. Back Pain, Nausea, Heart Attach, Depression)

D—Location of Medical Practitioner (e.g. City/ State/ or Country)

E—Tags (e.g. Golf, Infectious Disease, Duke University, Children)

F—Specialty (e.g. Cardiology, Oncology, Orthopedics, Pediatrics)

Thus popular searches may be various combinations such as:

1: Preferred language, price range, and health concern

2: Preferred language, price range, and location of medical practitioner

3: Preferred language, price range, and tags

4: Preferred language, price range, and specialty

5: Price range, health concern, and location of medical practitioner

6: Price range, health concern, and tags

7: Price range, health concern, and specialty

8: Price range, location of medical practitioner, and tags

9: Preferred language, health concern, tags,

10: Preferred language, health concern, specialty

11: Preferred language, health concern, and location of medical practitioner

Other search combinations are also possible, and often the user interface will be designed with appropriate checkboxes, radio buttons, or natural language interface to enable the users to rapidly and flexibly conduct searches as they see fit.

The invention claimed is:

1. A computer-implemented method of conducting Internet based telemedicine across at least two geopolitical zones comprising:
   a first geopolitical zone comprising:
   a healthcare practitioner, a first licensing authority, and a first legal authority;
      the first licensing authority, providing via the Internet, a certificate authorizing a healthcare practitioner to practice telemedicine in a first geopolitical zone;
      a second geopolitical zone, where the healthcare practitioner is not licensed to practice medicine, comprising:
   a patient, a second licensing authority, and a second legal authority;
      the healthcare practitioner via the telemedicine server, transmitting to the second licensing authority via the Internet, identifying information, the provided certificate, and a request for authorization to practice telemedicine in the second geopolitical zone;
      the telemedicine server, receiving from the second licensing authority via the Internet, a certificate reciting authorization by the second licensing authority for the healthcare practitioner to practice telemedicine in the second geopolitical zone for a predetermined amount of time, wherein the predetermined amount of time is the length of the telemedicine session;
      the telemedicine server, transmitting to an Internet-server-based database via the Internet, the certificate reciting authorization by the second licensing authority for the healthcare practitioner to practice telemedicine in the second geopolitical zone for the predetermined amount of time;
      the patient via the telemedicine server, transmitting to the first legal authority via the Internet, a request for a legal waiver for consent to a telemedicine session with an authorized healthcare practitioner from the first geopolitical zone;
      the telemedicine server, receiving from the first legal authority via the Internet, a legal waiver authorizing the patient to participate in a telemedicine session with the healthcare practitioner located in the first geopolitical zone;
      the telemedicine server, transmitting to the Internet-server-based database via the Internet, the patient's legal waiver, the patient's current medical condition and a request for available healthcare practitioners authorized to practice telemedicine in the second geopolitical zone;
      the patient via the telemedicine server, receiving from the Internet-server-based database via the Internet, the practitioner's identifying information.

2. The computer-implemented method of claim 1, wherein the Internet-server-based database further comprises the specialties and availability schedules of at least one of the healthcare practitioners from the first geopolitical zone.

3. The computer-implemented method of claim 2, in which the Internet-server-based database matches the patient's current medical condition with the specialties and availability schedules of at least one of the healthcare practitioners;
   the Internet-server-based database provides the matched specialties and availability schedules to the patient; and wherein the patients may use the matched specialties and availability schedules to select an appointment time to schedule a telemedicine session with at least one healthcare practitioner.

4. The computer-implemented method of claim 3, wherein the Internet-server-based database further comprises either the electronic health records or links to the electronic health records of at least some of the patients, and wherein after the patient schedules a telemedicine session with at least one healthcare practitioner, the patient's electronic health record or link to the electronic health record is transmitted to the healthcare practitioner.

5. The computer-implemented method of claim 3, wherein the Internet-server-based database additionally comprises audio-video link information required to establish audio and video communication between the patient and the healthcare practitioner, and the Internet-server-based database transmits the audio-video link information to the patient and the healthcare practitioner on or before the time of said scheduled telemedicine session.

6. The computer-implemented method of claim 5, wherein the Internet-server-based database additionally comprises a list of authorized interpreters and interpreter audio-video link information, and wherein upon request by the patient or the healthcare practitioner, the Internet-server-based database additionally schedules a session with the interpreter at the same time as the scheduled telemedicine session, and the Internet-server-based database exchanges audio-video link information between the interpreter, the healthcare professional, and the patient, so that the patient, the healthcare professional, and the interpreter may establish a simultaneous three-way audio video link during the scheduled telemedicine session.

7. The computer-implemented method of claim 1, further displaying a visual simulation of patient travel from the second geopolitical zone to the first geopolitical zone on the user interface.

8. The computer-implemented method of claim 1, further adjusting the IP address of the Internet-server-based database to conform with IP addresses associated with either the first geopolitical zone or the second geopolitical zone.

9. The computer-implemented method of claim 1, wherein the geopolitical zones are American states, and the healthcare professionals are physicians.

10. A computer-implemented method of conducting Internet based telemedicine across at least two geopolitical zones comprising:
    a first geopolitical zone comprising:
    a healthcare practitioner, a healthcare practitioner's profile, wherein the profile contains a specialty and an availability schedule, a first licensing authority, and a first legal authority;
       the first licensing authority, providing via the Internet, a certificate authorizing a healthcare practitioner to practice telemedicine in a first geopolitical zone;
       a second geopolitical zone, where the healthcare practitioner is not licensed to practice medicine, comprising:
    a patient, a second licensing authority, and a second legal authority;
       the healthcare practitioner via the telemedicine server, transmitting to the second licensing authority via the Internet, the healthcare practitioner's profile, the provided certificate, and a request for authorization to practice telemedicine in the second geopolitical zone;
       the telemedicine server, receiving from the second licensing authority via the Internet, a certificate reciting authorization by the second licensing authority for the healthcare practitioner to practice telemedicine in the second geopolitical zone for a predetermined amount of time, wherein the predetermined amount of time is the length of the telemedicine session;

the telemedicine server, transmitting to an Internet-server-based database via the Internet, the certificate reciting authorization by the second licensing authority for the healthcare practitioner to practice telemedicine in the second geopolitical zone for the predetermined amount of time and the healthcare practitioner's profile;

the patient via the telemedicine server, transmitting to the first legal authority via the Internet, a request for a legal waiver for consent to a telemedicine session with an authorized healthcare practitioner from the first geopolitical zone;

the telemedicine server, receiving from the first legal authority via the Internet, a legal waiver authorizing the patient to participate in a telemedicine session with the healthcare practitioner located in the first geopolitical zone;

the telemedicine server, transmitting to the Internet-server-based database via the Internet, the patient's legal waiver, the patient's current medical condition and a request for available healthcare practitioners authorized to practice telemedicine in the second geopolitical zone;

the patient via the telemedicine server, receiving from the Internet-server-based database via the Internet, at least one healthcare practitioner name, specialty, and availability schedule that matches the patient's current medical condition;

the patient via the telemedicine server, transmitting to the Internet-server-based database via the Internet, a selection for an available appointment with at least one healthcare practitioner;

the patient via the telemedicine server, receiving from the Internet-server-based database via the Internet, audio-video link information required to establish audio and video communication between the patient and the selected healthcare practitioner.

11. The computer-implemented method of claim 10, wherein the patient communicates with the Internet-based-server database via a computational device comprising: a video display screen, a user interface, a video camera, a microphone, and a speaker, wherein the patient may conduct said scheduled telemedicine session using the user interface of the computational device.

12. The computer-implemented method of claim 10, wherein the Internet-server-based database further comprises either the electronic health records or links to the electronic health records of at least some of the patients, and wherein after the patient schedules a telemedicine session with at least one healthcare practitioner, the patient's electronic health record or link to the electronic health record is transmitted to the healthcare practitioner.

13. The computer-implemented method of claim 10, wherein the Internet-server-based database additionally comprises a list of authorized interpreters and interpreter audio-video link information, and wherein upon request by the patient or the healthcare practitioner, the Internet-server-based database additionally schedules a session with the interpreter at the same time as the scheduled telemedicine session, and the Internet-server-based database exchanges audio-video link information between the interpreter, the healthcare professional, and the patient, so that the patient, the healthcare professional, and the interpreter may establish a simultaneous three-way audio video link during the scheduled telemedicine session.

14. The computer-implemented method of claim 10, wherein the patient may enter the legal waiver into the Internet-server-based database prior selecting the appointment time.

15. The computer-implemented method of claim 10, wherein the Internet-server-based database additionally accepts payment from the patient or third party payors, and disperses at least some of the payment to the healthcare practitioner.

16. The computer-implemented method of claim 15, wherein the payment from third party payors is made by at least one gift certificate.

17. The computer-implemented method of claim 10, wherein the healthcare practitioner communicates with the Internet-based-server database via a computational device comprising: a video display screen, a user interface, a video camera, a microphone, and a speaker, wherein the healthcare practitioner may conduct said scheduled telemedicine session using the user interface of the computational device.

18. A computer-implemented method of conducting Internet based telemedicine across at least two geopolitical zones comprising:

a first geopolitical zone comprising:
    a healthcare practitioner, a healthcare practitioner's profile, wherein the profile contains a specialty and an availability schedule, a first licensing authority, and a first legal authority;
    the first licensing authority, providing via the Internet, a certificate authorizing a healthcare practitioner to practice telemedicine in a first geopolitical zone;
    a second geopolitical zone, where the healthcare practitioner is not licensed to practice medicine, comprising:
a patient, a patient's electronic health records, a second licensing authority, and a second legal authority;
the healthcare practitioner via the telemedicine server, transmitting to the second licensing authority via the Internet, the healthcare practitioner's profile, the provided certificate, and a request for authorization to practice telemedicine in the second geopolitical zone;
the telemedicine server, receiving from the second licensing authority via the Internet, a certificate reciting authorization by the second licensing authority for the healthcare practitioner to practice telemedicine in the second geopolitical zone for a predetermined amount of time, wherein the predetermined amount of time is the length of the telemedicine session;
the telemedicine server, transmitting to an Internet-server-based database via the Internet, the certificate reciting authorization by the second licensing authority for the healthcare practitioner to practice telemedicine in the second geopolitical zone for the predetermined amount of time and the healthcare practitioner's profile;
the patient via the telemedicine server, transmitting to the first legal authority via the Internet, a request for a legal waiver for consent to a telemedicine session with an authorized healthcare practitioner from the first geopolitical zone;
the telemedicine server, receiving from the first legal authority via the Internet, a legal waiver authorizing the patient to participate in a telemedicine session with the healthcare practitioner located in the first geopolitical zone;

the telemedicine server, transmitting to the Internet-server-based database via the Internet, the patient's legal waiver, the patient's current medical condition, the patient's electronic medical record and a request for available healthcare practitioners authorized to practice telemedicine in the second geopolitical zone;

the patient via the telemedicine server, receiving from the Internet-server-based database via the Internet, at least one healthcare practitioner name, specialty, and availability schedule that matches the patient's current medical condition;

the patient via the telemedicine server, transmitting to the Internet-server-based database via the Internet, a selection for an available appointment with at least one healthcare practitioner;

the patient via the telemedicine server, receiving from the Internet-server-based database via the Internet, audio-video link information required to establish audio and video communication between the patient and the selected healthcare practitioner;

the healthcare practitioner via the telemedicine server, receiving from the Internet-server-based database via the Internet, a confirmation of an appointment and the patient's electronic medical record.

19. The computer-implemented method of claim 18, wherein the healthcare professional further enters information obtained from the telemedicine session into the electronic health record associated with the patient.

20. The computer-implemented method of claim 18, wherein an audio or audio-video record of the telemedicine session is entered into the electronic heath record associated with the patient.

* * * * *